(12) United States Patent
Bakos

(10) Patent No.: US 7,967,842 B2
(45) Date of Patent: Jun. 28, 2011

(54) INTEGRATED SECUREMENT AND CLOSURE APPARATUS

(75) Inventor: Gregory J. Bakos, Mason, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 1061 days.

(21) Appl. No.: 11/756,914

(22) Filed: Jun. 1, 2007

(65) Prior Publication Data

US 2008/0300547 A1    Dec. 4, 2008

(51) Int. Cl.
*A61B 17/04* (2006.01)
*A61B 1/00* (2006.01)

(52) U.S. Cl. .................. 606/232; 606/144; 600/104

(58) Field of Classification Search ............ 606/139, 606/144, 148, 151, 167, 213, 232, 153; 600/104
See application file for complete search history.

(56) References Cited

U.S. PATENT DOCUMENTS

| | | | | |
|---|---|---|---|---|
| 5,391,182 A | * | 2/1995 | Chin | 606/213 |
| 5,573,540 A | * | 11/1996 | Yoon | 606/139 |
| 6,117,150 A | * | 9/2000 | Pingleton et al. | 606/167 |
| 6,352,503 B1 | * | 3/2002 | Matsui et al. | 600/104 |
| 6,626,930 B1 | * | 9/2003 | Allen et al. | 606/213 |

* cited by examiner

*Primary Examiner* — Julian W Woo

(74) *Attorney, Agent, or Firm* — Porter, Wright, Morris & Arthur, LLP

(57) ABSTRACT

An integrated securement and closure apparatus uses mechanical fasteners disposed in access lumens located radially outwardly from a centrally disposed opening for an endoscope. The mechanical fasteners are used to secure the distal end of an overtube against and isolate a target area of tissue inside a patient. An incision is made in the isolated target and the mechanical fasteners are used to approximate the tissue of the incision following and surgical intervention.

6 Claims, 3 Drawing Sheets

INTEGRATED SECUREMENT AND CLOSURE APPARATUS

FIELD OF THE INVENTION

The present invention relates generally to surgical appliances, and more particularly to an integrated appliance for use in laparoscopic and endoscopic surgery. The invention will be specifically disclosed in a connection with an apparatus for use in both securing a surgical appliance to a tissue wall and in closing an incision created in a surgical intervention.

BACKGROUND

In recent years, there has been substantial interest in the development and application of minimally invasive surgical techniques. Minimally invasive surgical techniques have become increasingly popular because tissue damage from such techniques is minimal and the recovery time for patients undergoing such procedures is typically shorter than for procedures performed by conventional surgical techniques. For example, laparoscopic surgery techniques have made it possible to access to organs in the peritoneal cavity without the necessity of creating huge incision in the abdominal wall. Instead, far smaller and less invasive incisions in the abdominal wall are required when laparoscopic techniques are used. These much smaller and less invasive incisions enable patients to be discharged more quickly with less trauma and more cosmetically appealing results.

Substantial advancements are now underway to provide surgical access to the peritoneal cavity without providing any incision in the abdominal wall. This new technique, sometimes referred to as Natural Orifice Transluminal Endoscopic Surgery (also known by the acronym in a thing of beauty to you soon "NOTES"), provides access to organs located in the peritoneal cavity through a natural orifice of the body, as for example through the colon, throat or the vagina. This technique leaves no visible scars and minimizes post operative pain. In employing this technique, an endoscope is passed through a natural orifice of the body, such as the mouth or anus, and the endoscope is extended into a selected area of the digestive tract, such as the stomach or colon, that is proximally located relative to the abdominal structure of interest. An incision is then made in wall of the stomach or colon, and the endoscope is then passed through the incision to perform diagnostic or therapeutic interventions on a structure of interest located in the peritoneal cavity.

One potential problem with accessing the peritoneal cavity through the digestive system is the possibility of carrying contaminants from the digestive tract into the peritoneal cavity, either directly or on the instruments that are inserted through the luminal incision in the wall of the colon or stomach. It is, of course, highly desirable to avoid contamination of the peritoneal cavity, and to perform the diagnostic or therapeutic procedure in a sterile field. One method of reducing the risk of contamination is to use an overtube, that is, a tubular member positioned on the outside of the endoscope through which the endoscope is slidably movable. An open end of the overtube is secured to wall of the stomach or colon, and a luminal incision is performed inside the area defined by the overtube. The walls of the overtube then function to isolate the area in which the luminal incision is made from the remainder of the digestive tract. With the end of the overtube secured to the wall of the digestive tract, an endoscope is then extended through the end of the overtube and into the peritoneal cavity through the luminal insertion. With the endoscope inserted into the peritoneal cavity, operational instruments are then passed through a working channel in the endoscope to access to an organ of interest located in the peritoneal cavity upon which a diagnostic or therapeutic intervention is desired. One way of securing the end of the overtube to the wall of the stomach or colon is through the use of a vacuum. Unfortunately, securing the end of an overtube to the wall of a stomach or colon with a vacuum is not always fully reliable. The stomach wall, for example, is very flexible, and the seal between the end of the overtube and the stomach wall is easily lost whenever the stomach flexes or otherwise moves. When the seal between the end of the overtube and the stomach wall is lost, the luminal incision is no longer isolated from the remaining areas of the digestive track, and the passage of contamination through the luminal incision into the peritoneal cavity may occur. As a consequence, the sterility of the field in the peritoneal cavity in which the diagnostic or therapeutic intervention is occurring is compromised.

In addition to introducing contamination into the peritoneal cavity while the surgical intervention is being performed, substantial problems arise in connection with preventing contamination from entering the peritoneal cavity during and after removal of the endoscope and closure of the incision. In addition, closing gastric lumen incisions is frequently either time-consuming or very difficult, or both. For example, many clip appliers or capable of inserting only a single clip at a time, and the applier must be pulled out of the surgical slight and reloaded after each clip is inserted.

BRIEF SUMMARY

One example of the invention is an apparatus for attaching an endoscopic appliance to a wall of organ of a patient and defining a localized working area during an endoscopic procedure. The apparatus includes an elongated overtube having a proximal end for location externally of a patient and a distal end for abutment against an internal tissue of a patient. The overtube has a centrally disposed cavity extending from its proximal end to its distal end for permitting a repeatable passage of an endoscope into the patient. A plurality of access lumens are disposed radially outwardly from the centrally disposed cavity on the periphery of the overtube, and a tissue-engaging mechanism is disposed in each of the plurality of access lumens. Each of the tissue-engaging mechanisms is activatable from a location external to the patient and is operative, when the overtube is partially inserted in a patient, to extend outwardly from the access lumens to engage tissue areas of the patient at a plurality of locations radially outwardly from the centrally disposed cavity of the overtube. The tissue-engaging mechanisms are operative to secure the distal end of the overtube to the patient, thereby defining an enclosed localized working area at the end of the overtube through which an incision of into the internal tissue of the patient may be made. A suture is secured to each of the tissue-engaging mechanisms. The sutures are manipulatable from a location external to a patient and jointly operative with each other to approximate the tissue areas engaged by the tissue-engaging mechanisms following incision through the working area. According to another example of the invention, a vacuum port is provided at the distal end of the overtube. This vacuum port is in fluid communication with a vacuum source and is operative to selectively apply a suction against the organ wall to sealingly interface the distal end of the overtube with the organ wall.

According to another example of the invention, there are at least three lumens with tissue-engaging mechanisms.

In one exemplary form, the tissue engaging mechanism includes a T-tag fastener.

In another example of the invention, a method is provided for securing an elongated surgical appliance to an internal target tissue of a patient. The appliance has a central opening adapted to accommodate an endoscope and a plurality of access lumens that are located radially outwardly from the central opening. The method includes the steps of directing a distal end of the surgical appliance to a target tissue area within a patient, and with the distal end of the appliance in proximity to the target tissue, applying a plurality of mechanical fasteners from the access lumens into the target tissue area and using the mechanical fasteners to secure the distal end of the surgical appliance to the target tissue and to isolate the target tissue from surrounding tissue.

In another example of the invention, the target tissue is disinfected while the distal end of the surgical appliance is secured to the target tissue, and an incision in the target tissue. A surgical instrument is advanced through the incision and a surgical intervention on the opposite side of the target tissue while the surgical appliance is secured to the target tissue.

In another example of the invention, the incision is closed with same the mechanical fasteners used to secure the distal end of the surgical appliance to the target tissue, as the separated tissue is tied together sutures used to secure the distal end of the surgical appliance to the target tissue.

BRIEF DESCRIPTION OF THE DRAWINGS

While the specification concludes with claims which particularly point out and distinctly claim the invention, it is believed the present invention will be better understood from the following description taken in conjunction with the accompanying drawings, in which like reference numbers identify the same elements in which:

Reference will now be made in detail to certain exemplary embodiments of the invention, examples of which are illustrated in the accompanying drawings.

DETAILED DESCRIPTION OF EXEMPLARY EMBODIMENTS

Figure 1:
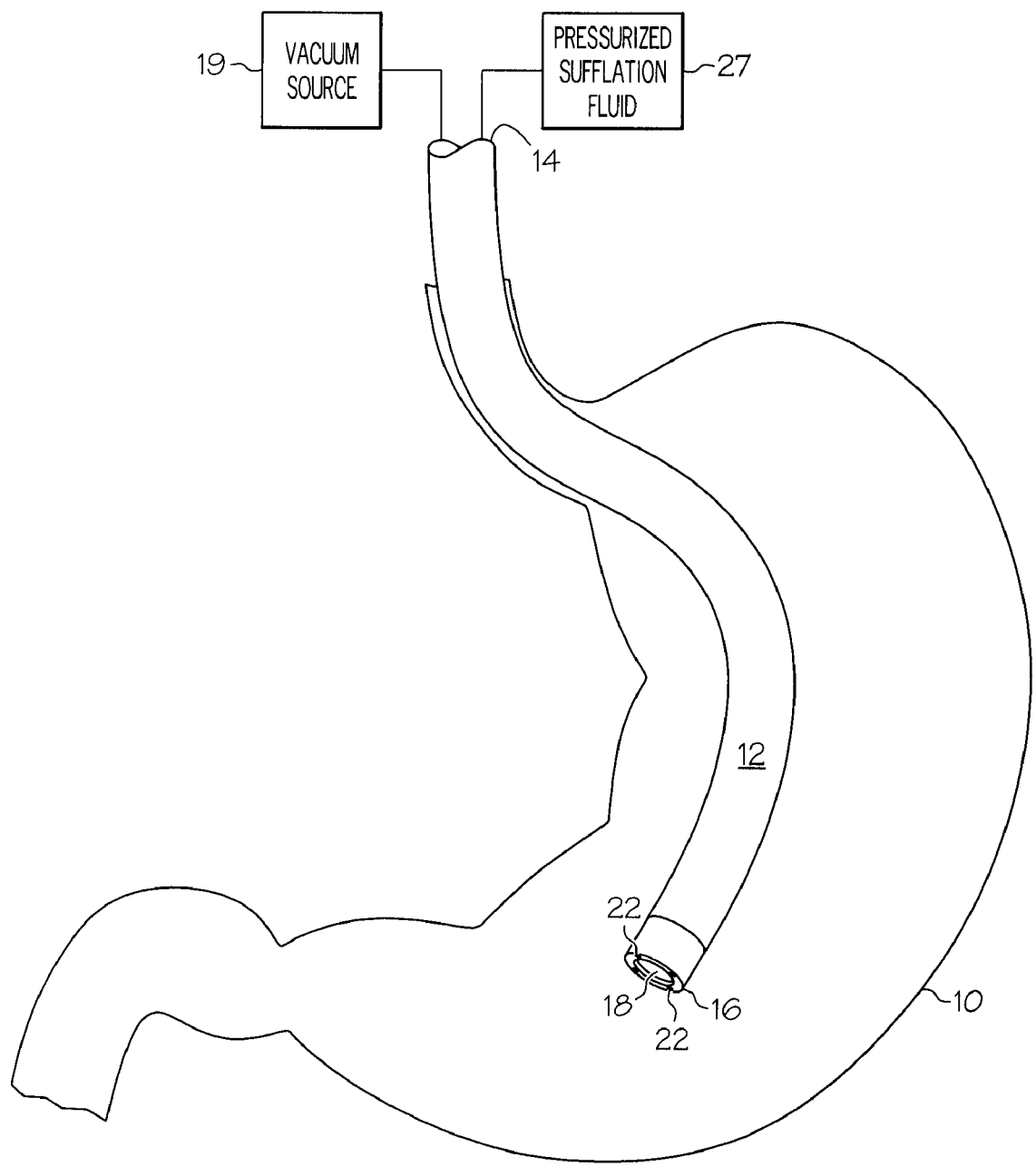
FIG. 1 is a perspective view of a human stomach with an overtube containing an endoscope inserted therein.

Referring now to the drawings, FIG. 1 schematically illustrates an organ 10, specifically illustrated as a stomach of a patient into which the distal end 16 of a flexible overtube 12 has been partially inserted. The overtube 12 is formed of highly flexible biocompatible material that slides through the digestive tract with a minimum of frictional resistance. It has an elongated, generally tubular configuration with a proximal end 14 located externally of the patient and a distal end 16 (as illustrated in FIG. 1) designed to be inserted into the digestive tract of a patient. In the illustration of FIG. 1, the distal end 16 of the overtube 12 is disposed in the patient's stomach. As those skilled in the art will readily appreciate, the overtube 12 provides a repeatable tubular passageway through which an endoscope or other instrumentation may be directed into the patient's body. In the specific illustration of FIG. 1, the overtube 12 has accessed the stomach 10 through the mouth of a patient. Depending upon the location of the specific portion of the body on which a diagnostic or therapeutic intervention is desired, access to the location may be made through alternative paths. For example, for a surgical intervention in the lower colon, or in a portion of the peritoneal cavity more closely positioned to the lower colon, access through the patient's anus may be preferable. Furthermore, in some applications, it may possible to access the targeted tissue without the necessity of extending the overtube through the digestive tract.

The overtube 12 includes a centrally disposed tubular passage 18 extending from the proximal end 14 to the distal end 16 which provides a repeatable path for an endoscope or other instrumentation. In the specifically illustrated embodiment, this passage 18 is used to slidably insert an endoscope 20 (not shown in FIG. 1, see FIGS. 2-6). The illustrated overtube has a plurality of circumferentially spaced access lumens 22 disposed radially outwardly from the centrally disposed passage 18. These access lumens 22 extend continuously from the proximal end 14 of the endoscope to the distal end 16 to provide working channels through which a surgeon can slide endoscopic tools or otherwise communicate with the distal end 16 of the endoscope.

Figure 2:
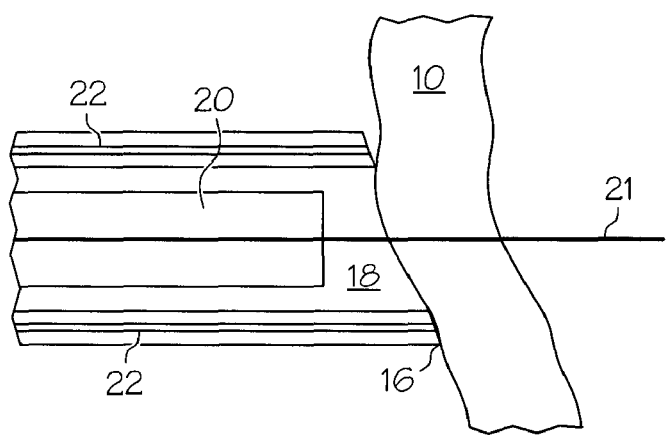
FIG. 2 is a schematic view showing the distal end of the overtube depicted in FIG. 1 engaging the stomach wall with a guide wire extending from the endoscope disposed within the overtube penetrating the stomach wall.

Referring now to FIG. 2, the distal end 16 of the overtube is shown after it has been manipulated from a location external to the patient so as to engage the distal end 16 of the overtube against a targeted area of the stomach 10, as is well known in the art. Depending upon the flexibility and ease with which the specific type of overtube 12 used can be manipulated, it may be desirable to first penetrate the target area with a guide wire 21 (see FIG. 2), and then use the guide wire 21 to slidingly direct the overtube 12 to the target location on the stomach wall 10 or other desired tissue. When moved to this position, a vacuum is applied to the passage 18 of the overtube 12 to sealingly engage the distal end 16 of the overtube 12 against the organ wall, which in the illustrated embodiment is depicted as the wall of a stomach 10. The source 19 for the vacuum might the vacuum available for a wall port (not shown) in a typical operating room, or any other suitable source. In any event, the source 19 is in fluid communication with the passage 18.

Figure 3:
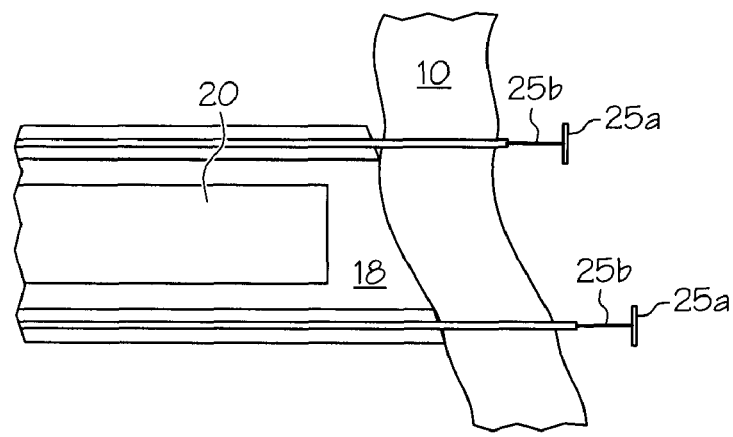
FIG. 3 is a schematic view of the distal end of the overtube depicted in FIG. 2 with tissue engaging mechanisms extending through the stomach wall to secure the overtube to the stomach wall.

While the application of a vacuum to the passage 18 is frequently sufficient to sealingly the engage the distal end 16 of the overtube 12, a vacuum induced seal between the end of the overtube 12 and the organ wall is occasionally lost, particularly when the organ wall is highly flexible, such as the stomach wall in the specifically illustrated embodiment. For this reason, according to one aspect of the present invention, a tissue engaging mechanism 25 is employed in each of the access lumens 22 for temporarily securing the distal end 16 of the overtube against the wall 10. The specific type of tissue engaging mechanism 25 illustrated in the drawings includes a T-tag fastener, which includes a T-type anchor 25a connected to a suture 25b. As those killed in the art will readily appreciate, the T-type anchor 25a of this type of fastener is oriented in the same general direction as the suture 25b when the fastener is in its non-deployed state. In this non-deployed state, the anchor 25a and suture 25b can be fitted in, and discharged from, each of the plurality of tubular shaped access lumens 22. Once the fastener 25 is discharged from the access lumen 22 (by a conventional T-tag applier, not shown), and tension is applied to the suture 25b, the anchor 25a rotates approximately 90 degrees to an orientation substantially perpendicular to the suture 25b, which relative orientation is depicted in FIG. 3. FIG. 3 shows two of these T-tag sutures 25 after they have been deployed from the access lumens 22 to penetrate the stomach wall 10, and rotated to a position in which the anchor 25a is substantially perpendicular to the attached suture 25b. Following deployment and attachment to the tissue 10, tension is applied to the sutures 25b to ensure sealing engagement between the distal end 16 of the overtube 12 and the stomach wall 10. With the distal end 16 of the overtube 12 secured to the organ wall 10 with the T-tag fasteners 25, the risk of accidental disengagement (and loss of seal) between the distal end 16 of the overtube 12 and the stomach wall 10 is virtually eliminated. Once the T-tag fasteners are in place, the vacuum for purposes of sealing that distal end 16 of the overtube 12 to the organ wall 10 may optionally be discontinued. Alternatively, the mechanical fasteners 25 might be used to secure the distal end 16 of the overtube 12 to the organ wall 10 without the assistance of any vacuum.

After the tissue engaging mechanism secures the distal end 16 of the overtube 12 to the stomach wall 10, an appropriate cleaning agent, such as a antibiotic or disinfectant fluid, optionally may be introduced into the target area defined by the overtube 12 to clean the surface of the organ. Cleaning is particularly appropriate when the organ wall to which the distal end 16 of the overtube 12 is being attached is located in an area of the body in which it has been exposed to bacteria or acids, such as in the colon or stomach. Any liquid cleaning agent may then be evacuated from the target area by the vacuum applied to the passage 18.

Figure 4:
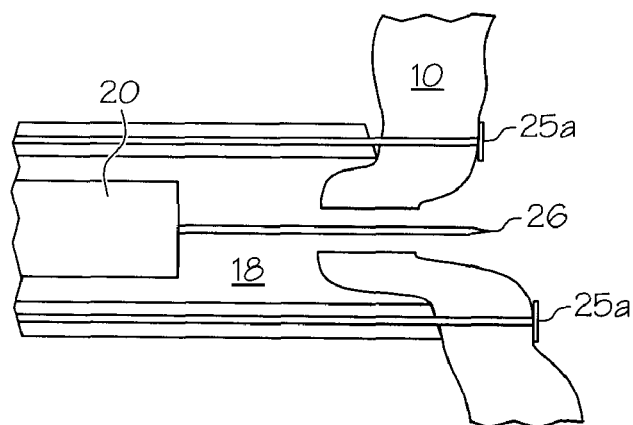
FIG. 4 is a schematic view of the distal end of the overtube with an incision device penetrating the stomach wall in the area defined by the overtube.
Figure 5:
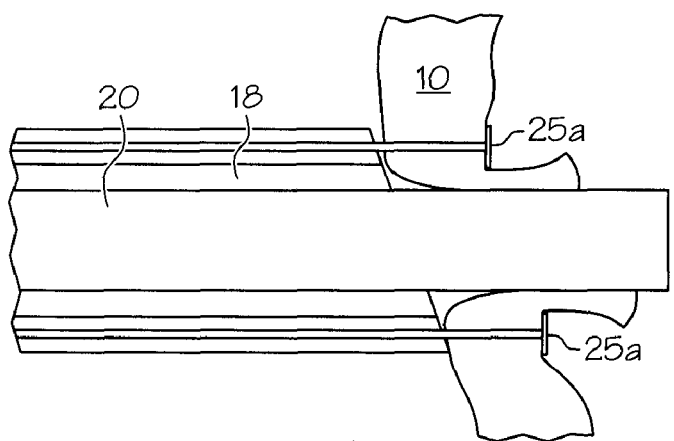
FIG. 5 is a schematic view of the distal end of the overtube depicted in FIG. 4 with the end does cope extended through the opening formed by the incision depicted in FIG. 4.

Once the surface of the organ wall 10 is cleaned, an incision is made through the organ wall 10 to allow the passage of the endoscope 20. The incision may be made with any standard and endoscopic cutting instruments, such as a standard needle knife 26 that might be directed to the target area through a working channel of the endoscope 20, as shown in FIG. 4. Once a small transmural incision is made, a standard pull type endoscopic surgical instrument can be used to extend the incision to an appropriate length. Alternatively, a balloon dilated catheter may be used to expand the incision. Depending upon the particular location, it also may be desirable to introduce an insufflation fluid, such as carbon dioxide, to expand the working space on the side of the organ wall 10 on the opposite side to which the overtube 12 is secured. This insufflation fluid might be introduced from a pressurized sufflation fluid source (schematically identified by the numeral 27) through the internal passage 18, or through an auxiliary channel in either the overtube of 12 or the endoscope 20. In either case, the insufflation fluid is delivered to the area through a port located at, or proximal to, the distal end 16 of the overtube 12. When the incision is of sufficient size to permit entry of the endoscope and the space on the opposite side of the organ wall 10 is sufficiently sufflated, the endoscope is axially advanced out of the overtube 12 into the peritoneal cavity, as depicted in FIG. 5, where the desired surgical intervention is performed. As shown in FIG. 5, the distal end 16 of the overtube 12 remains sealingly engaged with the organ wall 10 during the procedure performed with the endoscope 20 on the opposite side of the organ wall 10 to prevent fluids and contaminants from the stomach (or other organ) 10 from entering the peritoneal cavity during the procedure.

Figure 6:
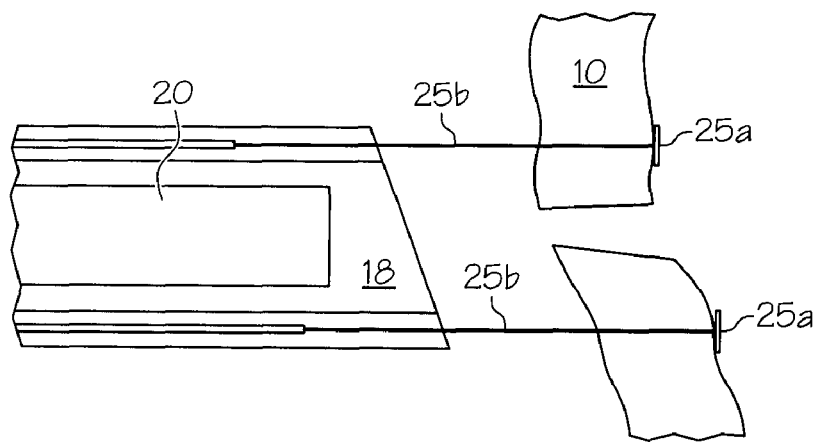
FIG. 6 is a schematic view depicting the withdrawal of the endoscope and showing sutures extending from the tissue engaging mechanisms.
Figure 7:
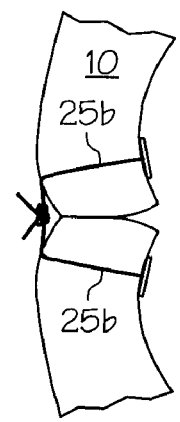
FIG. 7 is a schematic view of stomach area depicted in FIGS. 2-6 with the stomach tissue approximated by the sutures.

Once the surgical procedure in the peritoneal cavity is completed, the endoscope is retracted back through the overtube and withdrawn from the incision, as illustrated in FIG. 6. Advantageously, the same sutures used to secure the distal end 16 of the endoscope 12 to the stomach wall 10 remained at the incision site once the overtube 12 is withdrawn. These sutures, which are already secured to opposite sides of the incision, can then be pulled to approximate the opposite sides of the incision, as depicted in FIG. 7. In other words, the same connecting mechanism 25 used to secure the overtube 12 to the organ wall 10 can be used to close the incision. Using the same sutures 25b to close the incision that were used to secure the overtube 12 to the organ wall 10 eliminates both the need to apply sutures for closing the incision and the need for removing and replacing the tools in the working channels, permitting a substantial reduction in time and complexity of the procedure.

The foregoing description of the preferred embodiments of the present invention have been presented for purposes of illustration and description. It is not intended to be exhaustive or to limit the invention to the precise form disclosed. Obvious modifications or variations are possible in light of the above teachings. For example, while the exemplary embodiment in shown in connection with a transluminal NOTES endoscopic procedures, interluminal procedures and non-NOTES procedures, such as laparoscopic procedures, can be performed according to the principles of the invention. Furthermore, while the exemplary embodiment illustrated used T-tag fasteners as the tissue engaging structure, other types of tissue engaging structures might be used, as for example surgical screw tacks or other types of surgical clips. The embodiments were chosen and described to provide the best illustration of the principles of the invention and its practical application to thereby enable one of ordinary skill in the art to utilize the invention in various embodiments and with various modifications as are suited to the particular use contemplated. All such modifications and variations are within the scope of the invention as determined by the appended claims when interpreted in accordance with the breadth to which they are fairly, legally and equitably entitled. The drawings and preferred embodiments do not and are not intended to limit the ordinary meaning of the claims in their fair and broad interpretation in any way.

What is claimed is:

1. A method of securing an elongated surgical appliance to an internal target tissue of a patient, the appliance having a central opening adapted to accommodate an endoscope and a plurality of access lumens located radially outwardly from the central opening, the method comprising the steps of:
   directing a distal end of the surgical appliance to the internal target tissue of a patient;
   with the distal end of the appliance in proximity to the internal target tissue, applying a plurality of mechanical fasteners from the access lumens into the internal target tissue and using the mechanical fasteners to temporarily secure the distal end of the surgical appliance to the target tissue and to isolate a working area of the target tissue from surrounding tissue; and
   creating an incision in the working area after the distal end of the appliance is secured to the target tissue.

2. A method as recited in claim 1 further including the step of disinfecting the working area while the distal end of the surgical appliance is secured to the target tissue.

3. A method as recited in claim 1 further including the step of advancing a surgical instrument through the incision while the surgical appliance is secured to the target tissue and performing a surgical intervention on the side of the target tissue opposite the side to which the surgical appliance is secured.

4. A method as recited in claim 3 wherein the surgical instrument is an endoscope, and wherein the endoscope is advanced through the central opening of the surgical appliance and through the incision.

5. A method as recited in claim 4 further including the step of removing the endoscope from the incision following the surgical intervention, and closing the incision after removal of the endoscope with the mechanical fasteners used to temporarily secure the distal end of the surgical appliance to the target tissue.

6. A method as recited in claim 5 where in each of the mechanical fasteners include a suture, and the step of approximating the tissue includes tying the sutures together.

* * * * *